United States Patent
Edquist et al.

(10) Patent No.: US 9,801,717 B2
(45) Date of Patent: Oct. 31, 2017

(54) PROSTHETIC HEART VALVE HOLDER APPARATUS

(71) Applicant: St. Jude Medical, Inc., St. Paul, MN (US)

(72) Inventors: Brian James Edquist, Roseville, MN (US); Melinda Kaye Kovach, Plymouth, MN (US); Timothy John McGill, Minneapolis, MN (US); Julia Ann Schraut, Shoreview, MN (US); Matt Quest, Bothell, WA (US); Ralph J. Thomas, Champlin, MN (US); Scott Patrick Thome, St. Cloud, MN (US)

(73) Assignee: St. Jude Medical, Inc., St. Paul, MN (US)

( * ) Notice: Subject to any disclaimer, the term of this patent is extended or adjusted under 35 U.S.C. 154(b) by 0 days.

(21) Appl. No.: 15/148,500

(22) Filed: May 6, 2016

(65) Prior Publication Data

US 2016/0242903 A1   Aug. 25, 2016

Related U.S. Application Data

(63) Continuation of application No. 11/805,937, filed on May 24, 2007, now Pat. No. 9,333,076.

(51) Int. Cl.
*A61F 2/24* (2006.01)
*A61F 2/00* (2006.01)

(52) U.S. Cl.
CPC ............ *A61F 2/243* (2013.01); *A61F 2/0095* (2013.01); *A61F 2/2427* (2013.01); *A61F 2/24* (2013.01); *A61F 2/2409* (2013.01); *A61F 2/2412* (2013.01); *A61F 2250/0097* (2013.01)

(58) Field of Classification Search
CPC ............ A61F 2/2427; A61F 2250/0097; A61F 2/2412; A61F 2/2409
See application file for complete search history.

(56) References Cited

U.S. PATENT DOCUMENTS

| | | | |
|---|---|---|---|
| 2,674,286 A | 4/1954 | Carson | |
| 4,150,799 A | 4/1979 | Takada | |
| 4,683,883 A * | 8/1987 | Martin | A61F 2/2427 606/1 |
| 4,865,600 A * | 9/1989 | Carpentier | A61F 2/2427 623/2.11 |
| 5,089,015 A | 2/1992 | Ross | |

(Continued)

*Primary Examiner* — Gregory Anderson
*Assistant Examiner* — Christina Lauer
(74) *Attorney, Agent, or Firm* — Lerner, David, Littenberg, Krumholz & Mentlik, LLP

(57) ABSTRACT

Apparatus for use with a prosthetic heart valve includes a holder, to which the heart valve is releasably attached, and an elongated handle. The handle can be connected to the holder simply by pushing a distal end of the handle straight into a recess in the holder. After this has been done, the holder preferably releasable latches onto the handle, and the handle can also be rotated about its longitudinal axis to transmit torque to the holder (e.g., a rotatable portion of the holder). Rotation of such a rotatable portion of the holder can be used to deflect portions of the valve radially inward. This operation of a rotatable portion of the holder is preferably one-way only. The handle can be released from the holder at any time, and it can similarly be reconnected to the holder at any time.

20 Claims, 6 Drawing Sheets

(56) References Cited

U.S. PATENT DOCUMENTS

| | | | |
|---|---|---|---|
| 5,197,979 A | 3/1993 | Quintero et al. | |
| 5,290,300 A | 3/1994 | Cosgrove et al. | |
| 5,403,305 A | 4/1995 | Sauter et al. | |
| 5,560,487 A | 10/1996 | Starr | |
| 5,728,153 A | 3/1998 | Menkis et al. | |
| 5,800,531 A | 9/1998 | Cosgrove et al. | |
| 5,823,342 A | 10/1998 | Caudillo et al. | |
| 5,972,030 A | 10/1999 | Garrison et al. | |
| 6,199,696 B1 | 3/2001 | Lytle et al. | |
| 6,409,758 B2 | 6/2002 | Stobie et al. | |
| 6,416,547 B1 | 7/2002 | Erickson et al. | |
| 6,702,852 B2 | 3/2004 | Stobie et al. | |
| 6,723,122 B2 | 4/2004 | Yang et al. | |
| 2002/0013621 A1* | 1/2002 | Stobie | A61F 2/2427 623/2.11 |
| 2003/0125715 A1 | 7/2003 | Kuehn et al. | |
| 2006/0015177 A1 | 1/2006 | Quest et al. | |
| 2006/0241743 A1* | 10/2006 | Bergin | A61F 2/2409 623/2.11 |

\* cited by examiner

PROSTHETIC HEART VALVE HOLDER APPARATUS

CROSS-REFERENCE TO RELATED APPLICATIONS

This application is a continuation of U.S. application Ser. No. 11/805,937, filed on May 24, 2007, the disclosure of which is incorporated herein by reference.

BACKGROUND OF THE INVENTION

This invention relates to prosthetic heart valves, and more particularly to apparatus for use in holding such valves prior to and during implantation of the valve in a patient.

Prosthetic heart valves are used for replacing diseased and/or deficient valves in a patient's heart. For example, a patient's mitral and/or aortic valves may need to be replaced by such prostheses. One illustrative type of prosthetic heart valve includes animal tissue that has been treated to make it suitable for long-term use in a patient's body. Prior to implantation, such tissue valves may need to be stored in a liquid that preserves the tissue and keeps it flexible. During the implantation procedure, the prosthetic tissue valve is removed from the storage liquid, rinsed extensively to remove any vestige of that liquid, and then implanted in the patient, typically in an "open heart" surgical procedure. In addition, during the implantation procedure, it may be desirable to temporarily modify the shape of the prosthetic tissue valve in certain respects in order to facilitate getting the valve into place in the patient with good visualization and with good access for suturing the valve to native tissue of the patient. For example, this temporary shape modification may include deflecting free end portions of the commissural posts of the prosthetic tissue valve radially inwardly. This shape modification is preferably done just prior to the implantation procedure to avoid any part of the valve taking an undesirable "set" during prolonged deformation.

The above aspects of prosthetic tissue valve handling may be aided by associating the valve with a so-called holder. This association may include a suture connection between the valve and the holder. The holder can be used to hold the valve in its storage liquid. When it is desired to use (implant) the valve, a handle can be removably attached to the holder to remove the holder and valve from the storage liquid and to hold those components during the above-described rinsing. Attachment of the handle to the holder (or subsequent manipulation of the handle relative to the holder) may also be used to cause the above-described temporary deformation of the valve. The handle may also be used to place the holder and valve in the patient. The handle may be removed from the holder during suturing of the valve into the patient. The handle may then be re-attached to the holder so that when the sutures connecting the valve to the holder are cut, the handle can be used to remove the holder from the patient, leaving only the valve in the patient.

From the foregoing it will be seen that efficient, easy, and reliable handle and holder attaching, detaching, and re-attaching are highly desirable. Improvements to this (and related aspects) of prosthetic heart valve apparatus are therefore sought.

SUMMARY OF THE INVENTION

In accordance with the present invention, apparatus for use in conjunction with a prosthetic heart valve may include a holder, to which the heart valve is releasably attached, and an elongated handle having a distal end portion. The holder may have a receptacle portion that is adapted to removably receive the distal end portion by relative non-rotational motion of the holder and the handle along the longitudinal axis of the handle. The apparatus may include means for releasably latching the distal end portion of the handle into the receptacle portion of the holder. The apparatus may further include means for transmitting torque from the handle and about the longitudinal axis of the handle to the holder (e.g., a rotatable portion of the holder) while the handle is received in the holder.

If included, the rotatable portion of the holder may include a mechanism for inwardly deflecting certain portions of the valve (e.g., free end portions of commissural posts of the valve). If provided, such a mechanism preferably limits the extent to which the valve portions can be inwardly deflected by the mechanism. Also if provided, the above-mentioned mechanism is preferably operable only in a direction in which it deflects the valve portions inwardly. Another preferred feature of such a mechanism (if provided) is that it maintains inward deflection of the valve portions that it has imparted to those portions even if the handle is separated from the holder. The abovementioned mechanism may be operable on the valve portions to be deflected through sutures that are connected between the mechanism and those valve portions. These sutures may be severable to release the valve portions from inward deflection by the mechanism. A possible construction of this mechanism includes a pawl component and a ratchet component, with one of these components being on the rotatable portion of the holder, and the other of these components being on other structure of the holder.

If provided, the means for releasably latching may be automatically responsive to reception of the distal end portion of the handle in the receptacle portion of the holder to latch the handle to the holder. Again, if provided, the means for releasably latching may be manually operable to unlatch the handle from the holder.

If provided, the above-mentioned means for transmitting torque may include a non-circular cross section of the distal end portion. This means may further include a non-circular interior perimeter of the receptacle portion. The non-circular cross section may be receivable in the non-circular interior perimeter so that when the cross section is rotated about the longitudinal axis of the handle, a side of the cross section transmits torque about that axis to a side of the perimeter.

Further features of the invention, its nature and various advantages, will be more apparent from the accompanying drawings and the following detailed description.

DETAILED DESCRIPTION

Figure 1:
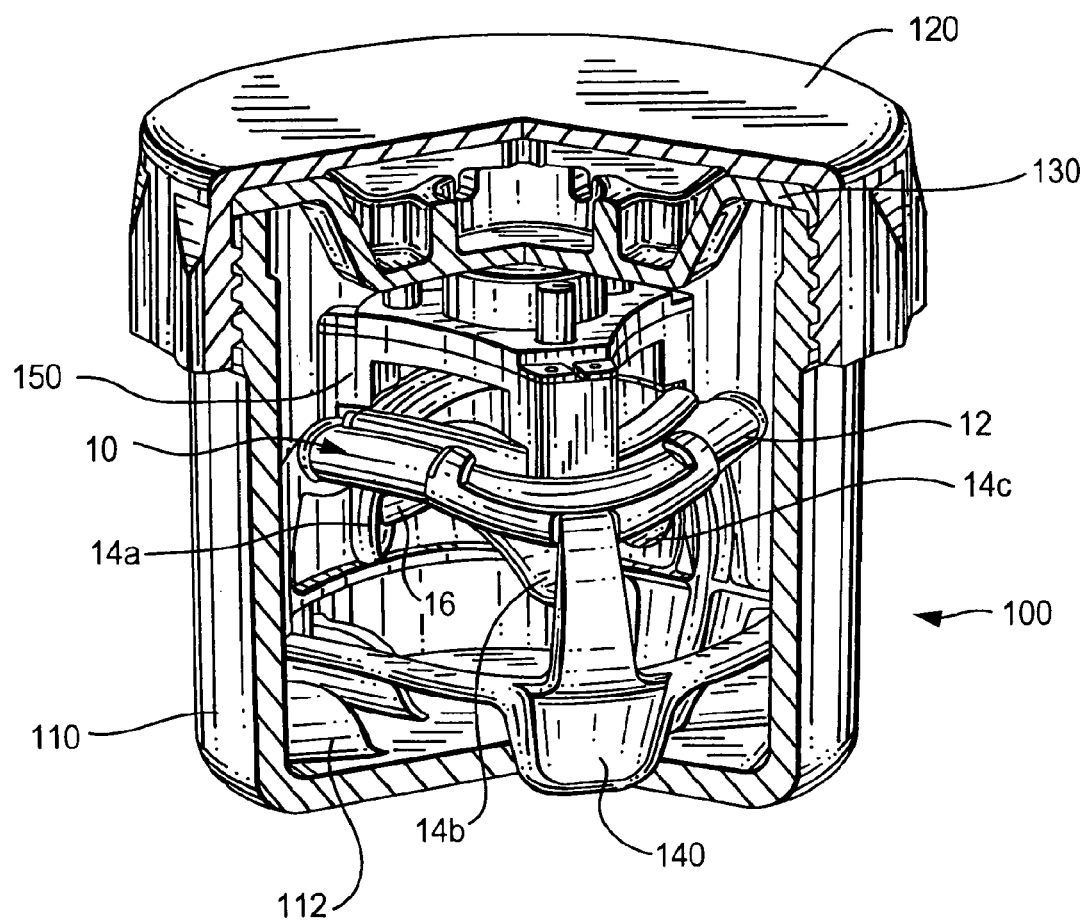
FIG. 1 shows an isometric view, partly in section, of illustrative known apparatus for holding a prosthetic heart valve during what may be relatively prolonged storage prior to use of the heart valve in a patient.

An illustrative prosthetic heart valve 10 and storage apparatus 100 for that heart valve are shown in FIG. 1. This FIG. shows known apparatus, but it provides useful context for the present invention. Heart valve 10 is a prosthetic mitral valve. It includes annular sewing cuff 12, three annularly spaced commissural posts or regions 14a, 14b, and 14c, and flexible (tissue) leaflet material 16 in the interior of the valve (i.e., bounded by sewing cuff 12 and regions 14).

Storage apparatus 100 includes jar 110, lid 120, lid liner 130, valve support 140, and valve holder 150. All of components 130, 140, and 150 (as well as valve 10) are inside jar 110. Lid 120 is removably attached to the top of jar 110 (e.g., by being threadedly connected to the jar). Valve support 140 rests on the bottom of jar 110 and is prevented from rotating relative to the jar by ribs 112 in the bottom of the jar engaging lower extremities of support 140. Upper extremities of support 140 engage sewing cuff 12 at several locations that are spaced around the sewing cuff. This engagement supports valve 10 in the position shown in the FIG.

Holder 150 rests on and is attached to valve 10 above support 140. For example holder 150 may be attached to valve 10 by an arrangement of sutures that is not visible in FIG. 1. The other components inside jar 110 are held down (lightly) by lid liner 130 bearing down on the top of holder 150.

Everything inside jar 110 is immersed in a liquid that the jar contains for such purposes as maintaining the tissue of valve 10 in usable condition. Note that in the valve-storage condition shown in FIG. 1, the commissural posts 14 of valve 10 extend substantially straight down from the upper annular portion of the valve. This is the relaxed or unstressed condition of the commissural posts.

When it is desired to use valve 10 in a patient, lid 120 and lid liner 130 are removed from jar 110. An elongated handle (not shown) is then threaded into a receptacle in the center of the upper part of holder 150. In addition to threadedly connecting the handle to holder 150, further rotation of the handle in the threading direction rotates a mechanism inside holder 150. Sutures (not shown) that pass between the tips or free ends of commissural posts 14 across the space between those tips are connected to this mechanism inside holder 150. Rotating this mechanism in the handle-threading direction wraps these sutures around a hub in this mechanism, which causes the lower tips of commissural posts 14 to deflect inwardly toward one another.

After the handle has been attached to holder 150 as described above, the handle can be used to pull holder 150, valve 10, and support 140 out of jar 110. This assembly of elements can remain together during rinsing of the valve. Eventually, support 140 is removed and the remaining handle and holder structure is used to aid in positioning valve 10 at the desired location in the patient. So that it will not be in the way during suturing of valve 10 into the patient, the handle may be unthreaded from holder 150. After valve 10 has been sutured in, the handle may be threaded back into holder 150, the sutures holding valve 10 to the holder may be" cut, and the handle may be used to withdraw holder 150 from the patient. Among other things, the immediately above-mentioned suture cutting releases the tips of commissural posts 14 to return to their unstressed condition (if that has not already happened as a result of unthreading the handle from holder 150.)

In accordance with the present invention, improved handle and holder structures are provided, which (among other advantages) allow the handle to be connected to or disconnected from the holder without threading or unthreading operations being required.

Figure 2:
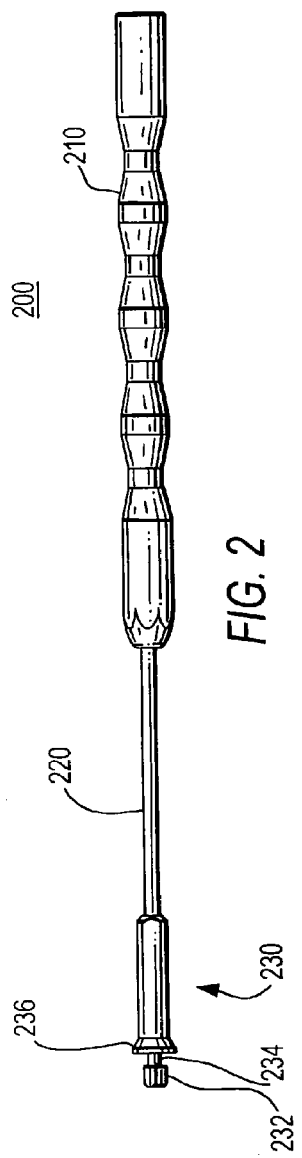
FIG. 2 is a simplified elevational view of an illustrative embodiment of apparatus in accordance with the invention.
Figure 3:
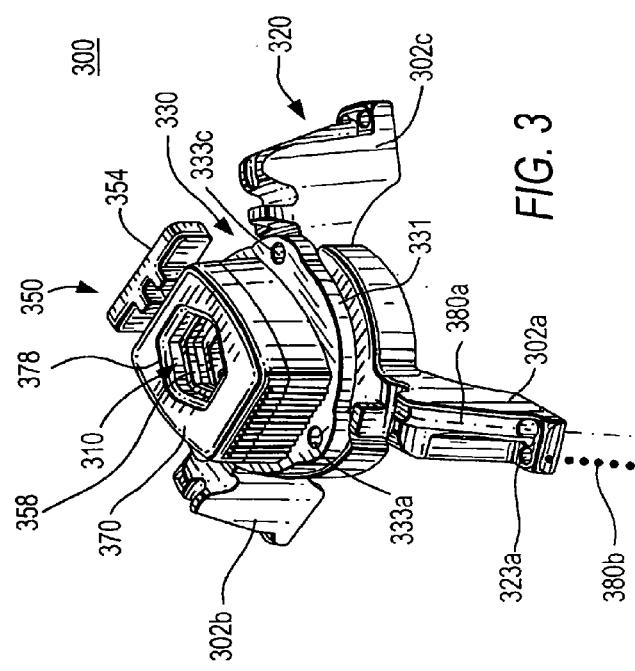
FIG. 3 is a simplified perspective or isometric view of an illustrative embodiment of additional apparatus in accordance with the invention.

An illustrative embodiment of a handle 200 in accordance with the invention is shown in FIG. 2. An illustrative embodiment of a valve holder 300 for use with handle 200 is shown in FIG. 3. Holder 300 is shown at a much larger scale in FIG. 3 than handle is shown in FIG. 2. An exploded view of holder 300 is provided in FIG. 4. Components 200 and 300 are used together by inserting what is the left-hand (distal) end of handle 200 as viewed in FIG. 2 vertically down into the aperture or recess 310 in the top of holder 300 as viewed in FIG. 3.

Handle 200 includes an elongated, proximal, grip portion 210; an elongated, intermediate, shaft portion 220; and a distal end portion 230. Grip portion 210 may be made of plastic and may be shaped to facilitate comfortable and secure holding in one hand of the user (e.g., a surgeon). Shaft portion 220 may be made of metal, which may be malleable if it is desired to allow the user to bend it laterally. Distal portion 230 includes a distal tip 232, which has a hexagonal cross section. Proximal to tip 232, distal portion 230 includes a section 234 having a cross section that is somewhat smaller than the cross section of tip 232. On the proximal side of reduced section 234, distal portion 230 has a radially outwardly extending flange 236. The cross section of flange 236 immediately proximal to reduced section 234 is preferably larger than the cross section of tip 232.

The size and shape of tip 232 are selected so that tip 232 will fit into holder aperture or recess 310 in a complementary way. Thus in this embodiment, tip 232 has a hexagonal cross section, and aperture or recess 310 also has a hexagonal interior perimeter that is slightly larger. Tip 232 should slide easily into aperture 310. But once tip 232 is in aperture 310, rotation of handle 200 about its longitudinal axis should apply torque to the holder component(s) in which aperture 310 is formed. This will be explained in more detail below in connection with the further discussion of holder 300.

Figure 4:
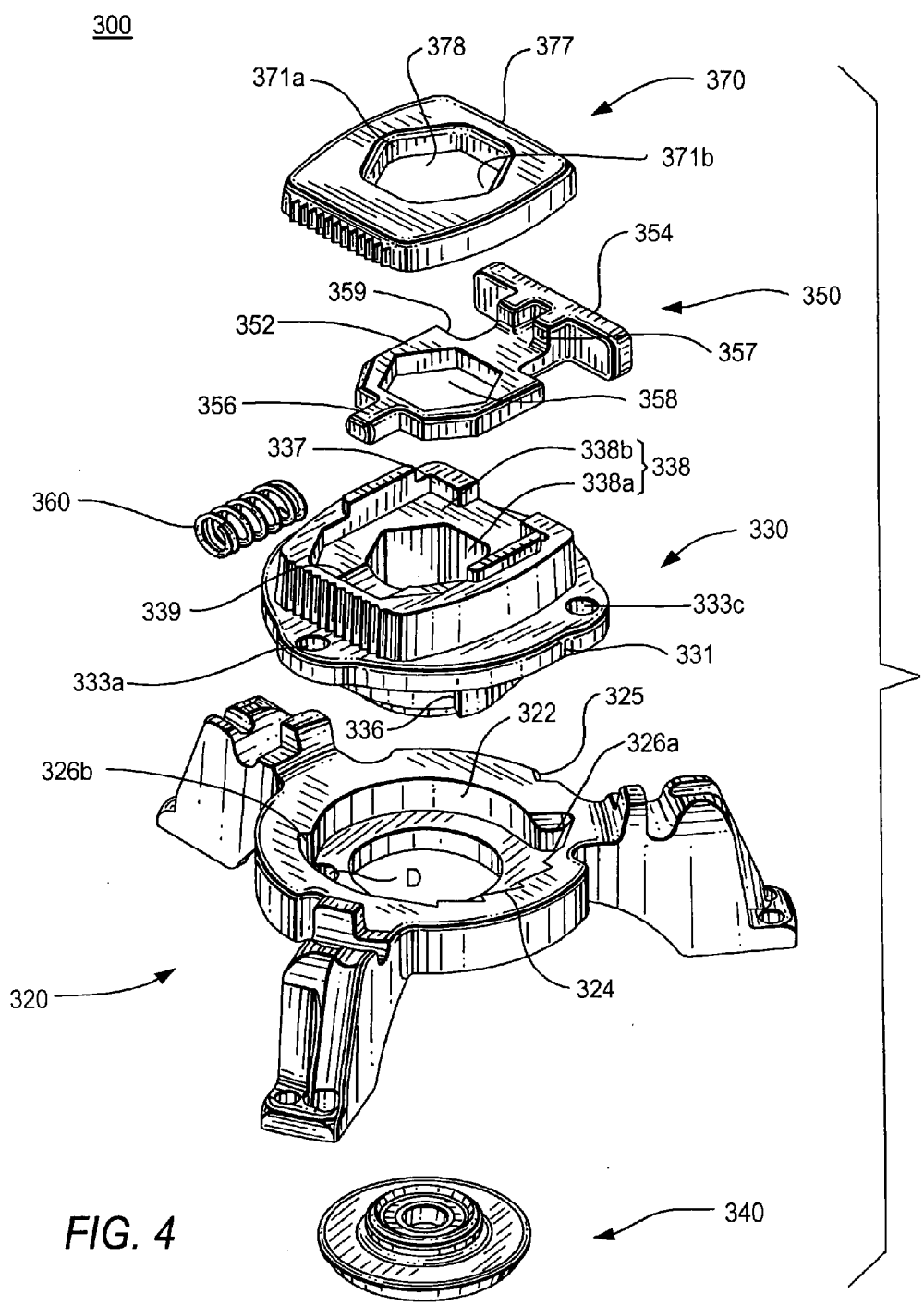
FIG. 4 is a simplified exploded view of what is shown in FIG. 3.
Figure 5:
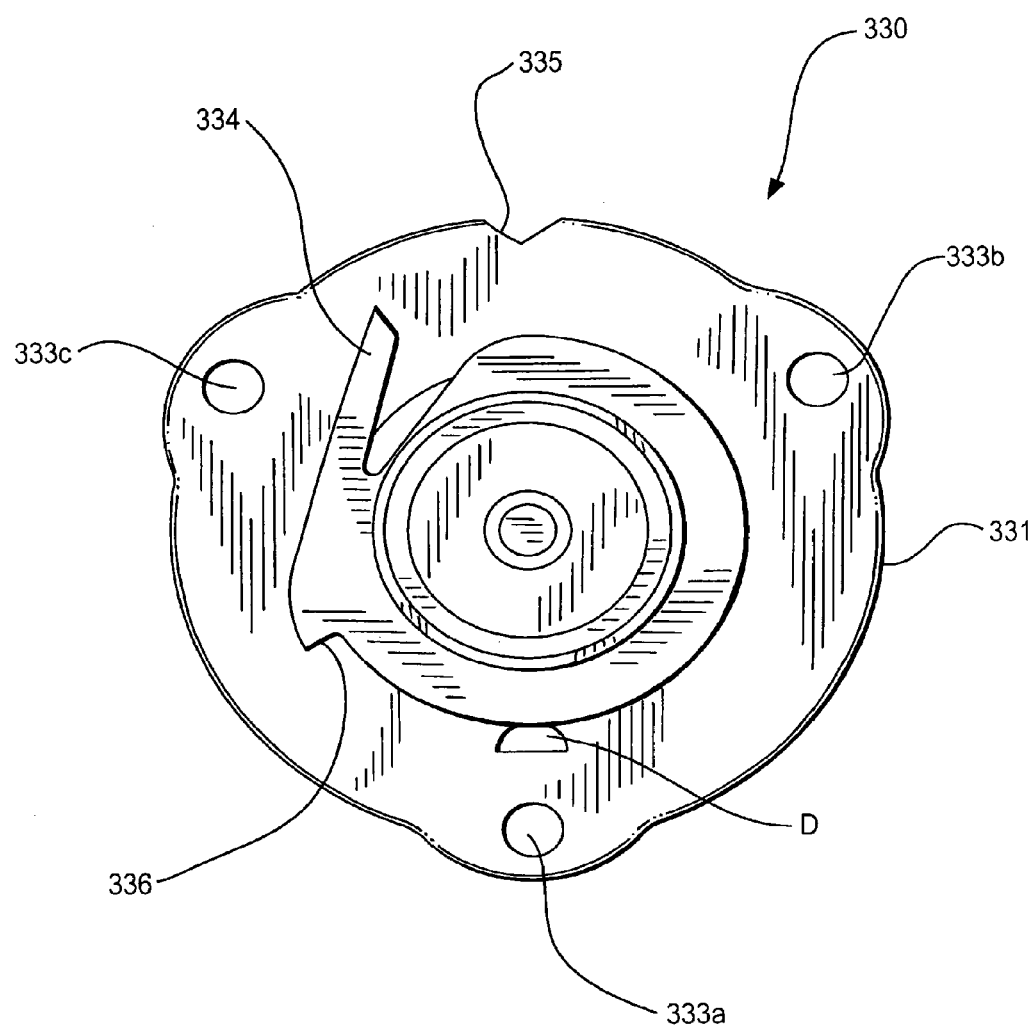
FIG. 5 is a simplified, bottom, plan view of one component of the apparatus shown in FIGS. 3 and 4.

As can be seen in FIG. 4, holder 300 includes a main body member 320, a main rotating member 330, a retainer member 340, a latch member 350, a spring 360, and a cap member 370. Note that when holder 300 is fully assembled, all of components 330, 340, 350, 360, and 370 rotate together (about a vertical central axis of the holder as viewed in either FIG. 3 or FIG. 4) relative to main body member 320. The lower part of main rotating member 330 is received in a recess 322 in the upper portion of main body member 320. A side wall of this main body recess includes a ratchet section 324 and two stop surfaces 326a and 326b. The portion of main rotating member 330 that fits into recess 322 includes a pawl finger 334 and a stop surface 336. (See also FIG. 5, which shows component 330 from below.) When main rotating member 330 is first assembled into main body member 320, member 330 is rotationally oriented relative to member 320 so that the free end of pawl 334 is close to or against stop surface 326a. This desired initial relative rotational relationship between elements 320 and 330 can be confirmed by axial alignment of notch 325 on element 320 and notch 335 on element 330. (This feature can also be used at any subsequent time to confirm that element 330 has not been rotated relative to element 320 prematurely.) After member 330 has been fully rotated (during use of the apparatus), stop surface 336 is against or close to stop surface 326b, and the free end of pawl 334 has passed at least several of the teeth of ratchet 324 but is still against or close to the stop surface or face of one of those ratchet teeth.

From the above description, it will be appreciated that after initial assembly of components 320 and 330, component 330 can only rotate in the clockwise direction relative to component 320 as viewed in FIG. 3 or FIG. 4. After such clockwise rotation, pawl and ratchet 324/334 prevent any significant reverse (counter-clockwise) rotation. In addition, the amount of clockwise rotation is limited by stop surface 336 coming into contact with stop surface 326b.

In assembled holder 300, component 330 is held in component 320 by securing retaining member 340 to the bottom of component 330. The bottom of component 330 is accessible for such securement of component 340 via the central aperture in the bottom of component 320. The outer diameter of component 340 is larger than the inner diameter of the bottom of the central aperture in component 320. Accordingly, after component 340 has been attached to component 330, components 330 and 340 can not come out of recess 322. (Component 330 is, however, rotatable relative to component 320 as described above.) Any suitable technique can be used for securing element 340 to element 330. Examples include welding, adhesive, a snap-fit interconnection, or any other mechanical and/or chemical positive retention method.

An upper part of main rotating member 330 has a recess 338 that includes two main parts: a lower hexagonal part 338a and an upper more tray-like part 338b. Recess part 338a forms a major portion of what is labeled as recess 310 in FIG. 3.

Latch member 350 has a portion 352 that can be received in recess portion 338b in component 330. This portion of latch member 350 includes a central, hexagonal aperture 358 that is similar in cross sectional size and orientation to recess portion 338a in component 330. Another (actuator) portion 354 of latch member 350 remains outside of component 330. The end of portion 352 that is most remote from actuator portion 354 includes a tab 356 that can be received in coil spring 360. Coil spring 360 is also receivable in the upper portion 338b of the recess 338 in component 330. When latch member 350 is assembled in recess 338 with spring 360, the spring is around tab 356 and somewhat compressed between an edge of component 350 and a wall portion 339 of recess 338. Accordingly, spring 360 resiliently urges component 350 to move relative to component 330 in the direction of latch actuator portion 354. Component 350 fits sufficiently loosely in recess portion 338b so that component 350 can move back and forth relative to the axis of axial compression/relaxation of spring 360. Travel of component 350 in the spring-relaxation direction is limited by component 350 shoulders 359 contacting recess 338b shoulders 337. Travel of component 350 in the spring-compression direction is limited by component 350 shoulders 357 contacting an edge 377 of cover member 370 (described in more detail below).

After elements 350 and 360 have been assembled in recess 338 as described above, that assembly is made permanent by placing cover member 370 over the top of recess 338 and the components 350 and 360 therein. Cover 370 does not interfere with the above-described back and forth motion of component 350 relative to component 330 (and now also relative to component 370), except for cover edge 377 cooperating with component 350 shoulders 357 to stop motion of component 350 in the spring-compression direction as described in the preceding paragraph. Again, any suitable technique can be used for securing cover 370 to component 330. For example, any of the techniques mentioned above for securing elements 330 and 340 together can be used for securing elements 370 and 330 together. The same technique can be used for both of these operations, or different techniques can be used for each operation.

Although apertures 338a and 358 are of approximately the same size, shape, and orientation, they can be either vertically aligned or misaligned, depending on whether or not latch member 350 has been shifted inwardly relative to elements 330 and 370. If latch member 350 has not been shifted in, apertures 338a and 358 are slightly misaligned in the vertical direction. If latch member 350 has been shifted in, apertures 338a and 358 are vertically aligned with one another.

Cover 370 has a central aperture 378 that is made up of two half-hexagons that are joined by short sides 371a and 371b. Aperture 378 forms the upper portion of what is called recess 310 in FIG. 3. Sides 371a/b are parallel to the direction of travel of latch member 350 in recess 338b. The half-hexagon of recess 378 that is closer to spring 360 is substantially directly above and has the same size and orientation as the corresponding portion of aperture 338a. The half-hexagon of aperture 378 that is closer to actuator portion 354 is directly above and has the same size and orientation as the corresponding portion of aperture 358 when latch member 350 is in its outer-most position relative to component 330. Note also that the upper portion of aperture 378 is inclined inwardly toward the lower portion of that aperture. This provides a lead-in for insertion of the distal end of holder 200 into the aperture in holder 300. The slight enlargement of aperture 378 into an octagon gives the distal end of holder 200 full access to aperture 358 in latch member 350 even when latch member 350 is in its outer-most position relative to elements 330 and 370. After the distal end of handle 200 has been inserted into aperture 358, the enlargement of aperture 378 allows the distal end of holder 200 to shift latch member 350 inwardly relative to components 330 and 370 as the distal end of holder 200 continues down into aperture 338a. This inward shifting of latch member 350 adds compression to spring 360.

Handle tip 232 and/or the upper portion of aperture 358 may be tapered or inclined in order to facilitate the above-described automatic shifting of latch member 350 (by cam-and-cam-follower-like cooperation of elements 232 and 358). Recess 338a is deep enough to allow tip 232 to pass all the way through apertures 378 and 358 and to be completely received in feature 338a.

When the reduced section 234 of handle 200 reaches the plane of latch member 350, latch member 350 is urged by spring 360 to snap back to its condition in which it is more outward relative to members 330 and 370, and in which aperture 358 is again somewhat misaligned with aperture 338a in the direction along the longitudinal axis of handle 200. As a consequence, a portion of the structure of latch member 350 adjacent to aperture 358 enters the channel that surrounds the reduced portion 234 of handle 200 and holds or latches holder 300 to the handle. This latching action is preferably accompanied by an audible sound, which provides feedback to the user that the handle and holder have latched together. Latching of the handle and holder together may also be accompanied by the distal surface of handle flange 236 coming into contact with the top of holder 300 to increase the stability of the connection between the handle and the holder.

Handle 200 can be released from holder 300 at any time by manually pressing in on actuator portion 354. This shifts member 350 so that aperture 358 becomes substantially aligned with feature 338a. Holder 300 is thereby no longer latched to handle 200, and handle 200 can accordingly be pulled out of recess 310.

As long as handle 200 is in recess 310 (e.g., while holder 300 is latched onto the distal end of handle 200 as described above), rotation of handle 200 in the proper direction about its longitudinal axis can be used to rotate components 330, 340, 350, 360, and 370 (relative to component 320) by the same amount in the same direction. Such rotation is, of course, subject to the constraints imposed by features 324, 334, 326, and 336 as described above. Note that there is a two-way positive rotational interconnection between handle 200 and holder components 330, etc., so that constraints on rotation of components 330, etc., act as identical constraints on rotation of handle 200.

The purpose of rotating components 330, etc., relative to component 320 is the same as in the FIG. 1 prior art. In particular, this purpose is to deflect the tips or free ends of valve commissural posts 14 radially inwardly. Each pair of such commissural tips has a suture passing through those tips and across the space between those tips. (These sutures have been additionally described earlier in this specification. They are shown in representative part at 380a and 380b in FIG. 3.) One end of each of these three sutures is tied to a respective one of three apertures 333a, 333b, and 333c in a flange 331 that extends around the outside of component 330 above component 320. The routing of the adjacent portion of one representative one of these sutures is shown by the chain-dotted line 380a in FIG. 3. (Dotted line 380b in FIG. 3 shows the other end of a different representative one of these sutures coming up from the valve and being attached to holder component 320 at the aperture 323a in that component.) Accordingly, when component 330 is rotated (by handle 200) in the clockwise direction in FIG. 3, component 330 will pull up on and take up some of each of the three suture portions that are attached to component 330 at apertures 333. This taking up of these sutures (which is somewhat like wrapping these suture portions) shortens the remainder of each suture that is still available for passing through and between the commissural tips. The result is inward deflection of the commissural tips by the sutures. Such inward deflection of the commissural tips may be helpful for such purposes as getting the valve into the proper position in the patient, better exposing the sewing cuff of the valve for suturing to the patient's native tissue, etc. Once the commissural tips have been thus deflected in, that deflection is irreversible except by cutting the sutures 380 that are involved in that deflection. The mechanism of holder 330 maintains the inward deflection of the commissural tips until those sutures are thus cut. Handle 200 can be removed from its connection to holder 300 as described in more detail below with no effect on the operation of holder 300 to keep the commissural tips deflected in.

It will be noted that, because of the operation of pawl and ratchet 324/334 and stop surfaces 326b/336, after rotatable portion 330 has been rotated relative to main body portion 320 as described above, no further relative rotation in either direction is possible. Accordingly, in the latter condition of the apparatus, any further torque on handle 200 in either direction about its longitudinal axis is transmitted through component 330 to component 320. Torque on handle 200 can therefore now be used to change the rotational orientation of the entire apparatus, including the valve on holder 300 (e.g., in the patient prior to suturing the valve to the patient). This may be desirable to help the surgeon give the valve the proper rotation relative to the patient's native tissue structure prior to suturing the valve into the patient. Because handle 200 is not threaded into holder 300, there is no possibility that torque (clockwise or counter-clockwise) on handle 200 will loosen the connection between handle 200 and holder 300.

After the valve (on holder 300 and handle 200) has been properly positioned in the patient, the surgeon may wish to remove handle 200 from the field of the surgical procedure. This may be desired, for example, to better clear the field for suturing the valve into the patient. Handle 200 can be removed by manually pressing in on actuator portion 354. This brings aperture 358 into substantial alignment with feature 338a, which unlatches handle 200 from holder 300 and allows the handle to be pulled out of holder recess 310. As noted above, such removal of handle 200 has no effect on the operation of holder 300 to maintain the tips of commissural posts 14 deflected radially inwardly.

After the valve (or at least its sewing cuff) has been sutured into the patient, the sutures like 380a and 380b that are maintaining the inward deflection of portions of the valve and/or otherwise holding the valve to holder 300 may be cut. This releases the inwardly deflected portions of the valve to resiliently return to their undeflected positions (to the extent permitted by now-adjacent tissue of the patient). Holder 300 is also released from the valve and can be removed from the patient. If desired, handle 200 can be reinserted into holder 300 to facilitate retrieval of the holder from the patient. Such handle reinsertion can be similar to the earlier-described initial insertion of handle 200 into holder 300.

It will be appreciated that among the advantages of the present invention is the fact that it avoids the need to screw or thread handle 200 into holder 300 to connect the handle to the holder. Instead, such a connection can be made much more rapidly by simply pushing the distal end of handle 200 straight into holder 300. It is not necessary to push in on actuator portion 354 of latch member 350 to make the connection between handle 200 and holder 300. Handle 200 can also be disconnected from holder 300 more rapidly than the previous threaded holder design. No unthreading or unscrewing is required. All that is required is to release the latch by pushing in on actuator surface 354. Handle 200 can then be immediately pulled straight out of the recess 310 in holder 300. Another advantage of the present invention is that it can provide positive but releasable latching between handle 200 and holder 300 when those two components are put together. Such latching is either not provided or would be more difficult to provide with threaded connection between the handle and the valve holder. Still another advantage of the invention is that it can provide an audible confirmation when latching between handle 200 and holder 300 has been effected. The source of this audible indication is the abrupt shifting of latch member 350 into the handle channel that surrounds reduced portion 234.

Figure 6:
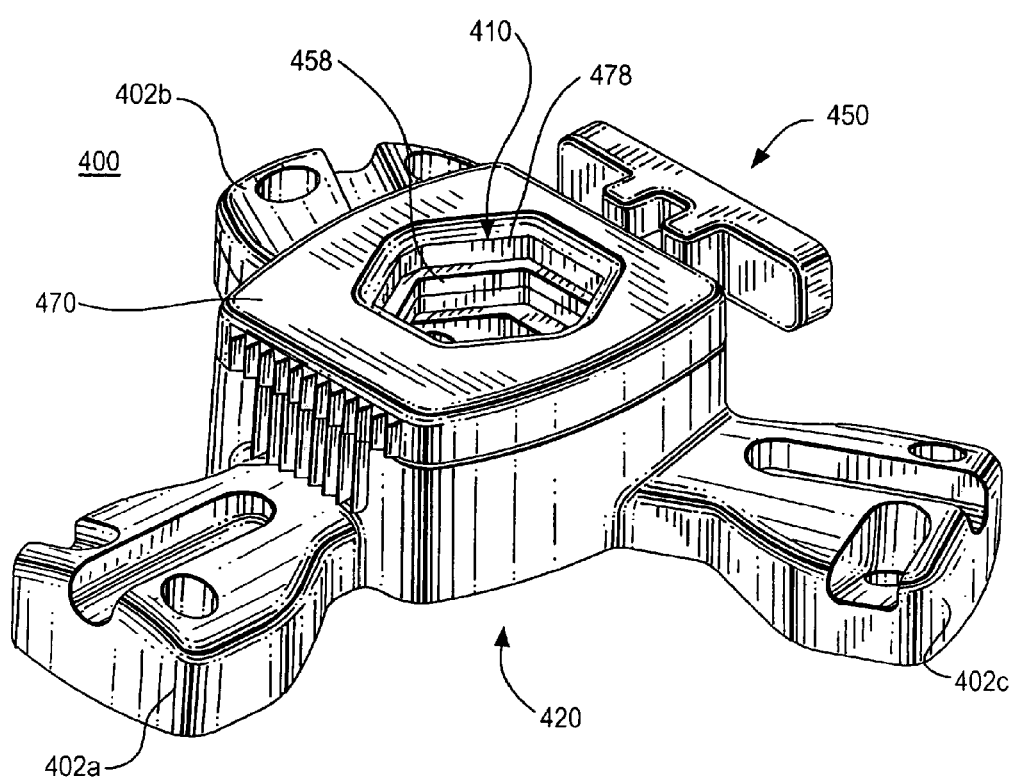
FIG. 6 is a view similar to FIG. 3 for another illustrative embodiment of the invention.
Figure 7:
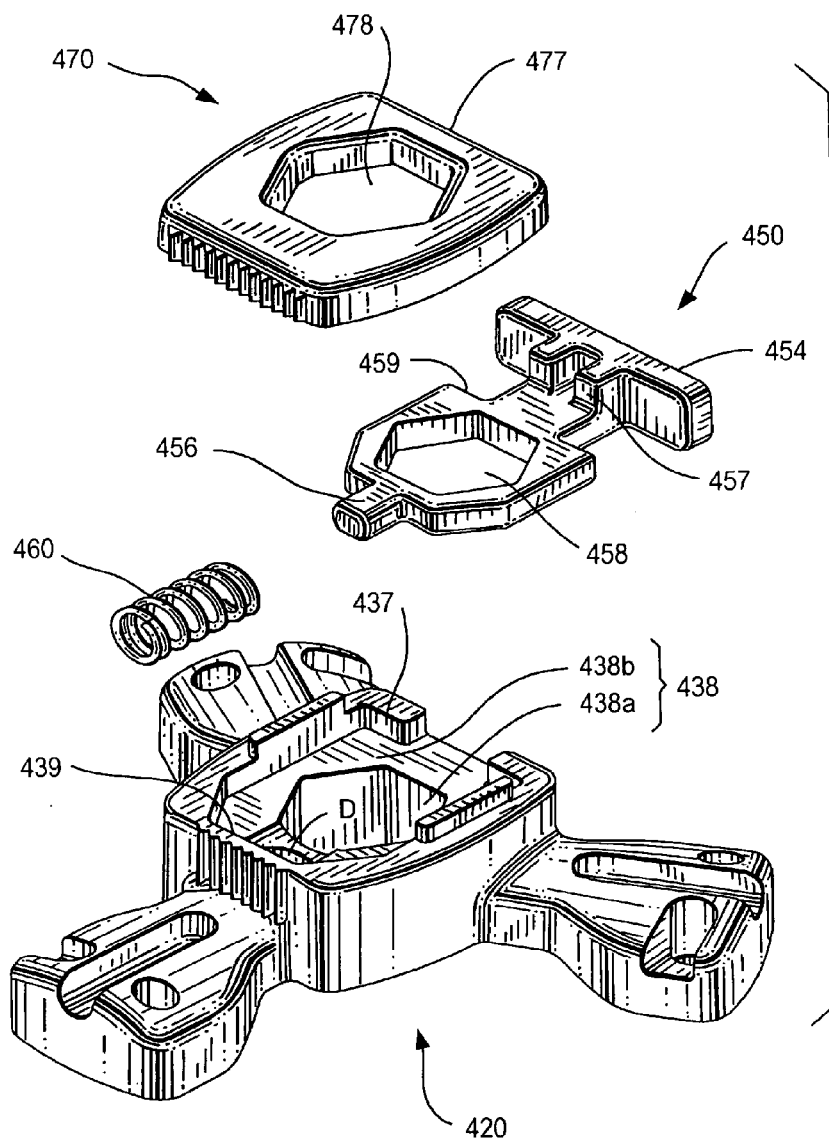
FIG. 7 is a view similar to FIG. 4 for the embodiment of FIG. 6.

FIGS. 6 and 7 show an illustrative alternative embodiment of the invention that is adapted for use with a prosthetic aortic valve or the like. To simplify the discussion, all prosthetic valves that are basically like aortic valves will be referred to simply as aortic valves. A prosthetic aortic valve is typically placed in a patient with the free ends or tips of the commissural posts of the valve closer to the surgeon, and with the fully annular portion of the valve (including the sewing cuff) farther from the surgeon. This means that an aortic valve is upside down as compared to the valve 10 that is shown in FIG. 1. The free ends of the arms 402a-c of holder 400 (FIGS. 6 and 7) therefore bear on the tips of the commissural posts of an associated aortic valve, and the remainder of the valve extends down below holder 400. Unlike holder 300, holder 400 is not capable of drawing these portions of the valve radially inwardly. Holder 400 merely holds the associated prosthetic aortic valve in a substantially fixed condition. Sutures are used to hold the valve to holder 400. The sutures are cut by the surgeon when it is desired to release the valve from the holder.

For present purposes, the major difference between holder 400 and holder 300 is that holder 400 does not include any relatively rotatable parts. In other respects pertinent to the present invention holder 400 can be similar to holder 300. For example, holder 400 can be used with the same handle 200 that has been described above, and that handle can be inserted into or removed from holder 400 in exactly the same way that it is inserted into and removed from holder 300. Parts and features of holder 400 that, for purposes of the present invention, are similar to parts and features of holder 300 have reference numbers in FIGS. 6 and 7 that are increased by exactly 100 from the reference number of the similar part or feature in the earlier FIGS. It will be noted in connection with FIGS. 6 and 7 that certain features that were associated with part 330 in holder 300 are associated with part 420 in holder 400. This is because holder 400 has no rotatable part like part 330 in holder 300. These features that are associated with part 420 (rather than with a rotatable part) include aperture 438 (including both of its portions 438*a* and 438*b*) and surfaces 437 and 439.

Because of the strong resemblance of holder 400 to holder 300, it will not be necessary to describe holder 400 in as much detail as holder 300 was described. Latch member 450 (similar to latch member 350 in holder 300) fits in the upper portion 438*b* of recess 438 in part 420. Spring 460 (similar to spring 360 in holder 300) fits around tab 456 and resiliently biases latch member 450 away from surface 439. Stop surfaces 437 and 459 cooperate to stop outward motion of latch member 450. Stop surfaces 457 and 477 cooperate to stop inward motion of latch member 450. Cover member 470 (similar to cover member 370 in holder 300) fits on member 420 over components 450 and 460 and keeps those components in the recess portion 438*b* of member 420.

Spring 460 resiliently biases latch member 450 so that feature 458 is normally somewhat eccentric to feature 438*a*. This is the condition of the apparatus that latches holder 400 to the received distal end of handle 200. Latch member 450 can be manually shifted toward spring 460 by pressing in on actuator surface 454. This can be done to bring feature 458 into alignment or registration with features 438*a*. When this is done, handle 200 is no longer latched in holder 400 and the handle can accordingly be pulled out of the holder. Pushing handle 200 into recess 410 also temporarily shifts feature 458 into alignment with features 438*a*. After the distal, hexagonal, end 232 of handle 200 has passed through aperture 458, latch member 450 automatically snaps back to the position in which feature 458 is eccentric to feature 438*a*, thereby automatically latching handle 200 in holder 400.

Note that any time handle 200 is engaged in holder 400, torque on handle 200 about its longitudinal axis is transmitted to holder 400 and the associated prosthetic aortic valve. Accordingly, such torque on handle 200 can be used to rotate holder 400 and the associated valve, e.g., for such purposes as getting the valve to the proper rotational position relative to the patient's native tissue. Because handle 200 (whether clockwise or counter-clockwise) does not thread into or out of holder 400, there is no possibility that such torque on handle 200 will loosen the connection between handle 200 and holder 400.

A few other possible features that can be included in apparatus in accordance with the invention will now be mentioned. Latch member 350/450 (especially actuator portion 354/454) can be of a different color than the rest of holder 300/400 to call attention to it as an actuatable part. Vertical ribs or other surface texturing can be provided on the outer surface of actuator 354/454 and the diametrically opposite outer surface of elements 330/370/420/470 to suggest and facilitate manual or forceps contact with these surfaces. (The vertical ribs referred to are visible on elements 330/370/420/470. They would be similar on actuator 354/454, but they are not visible in the accompanying FIGS. because the relevant actuator surface faces generally away from the viewer in these FIGS.) One or more vertical drain holes may be provided in elements like 320, 330, and 420 to facilitate drainage of valve storage liquid and valve rinsing liquid from inside holder 300/400. Examples of such drain holes are shown at reference letter D in several of the accompanying FIGS. Especially in the case of holder 400, the undersides of arms 402 may be shaped to complement and receive the tops of the commissural posts of the associated valve.

It will be understood that the foregoing is only illustrative of the principles of the invention, and that various modifications can be made by those skilled in the art without departing from the scope and spirit of the invention. For example, although complementary hexagonal shapes are shown for features 232 and 310/410, it will be understood that any of many other shapes can be used instead if desired. All that is required is that the shape(s) employed permit substantially linear or axial (non-rotational) association and disassociation of the handle and holder, and that while the handle and holder are associated, torque (about the axis along which the association has been established) can be transmitted from the handle to the holder. In general, such torque transmission can be accomplished by employing non-circular cross sections for the mating portions of the handle and the holder (i.e., the recess in the holder that receives the distal end of the handle). In the illustrative embodiments that have been shown and described in detail above, these non-circular cross sections are hexagonal. But this is only an example, and many other non-circular cross sections can be used instead if desired. Many other such modifications within the scope of the invention will occur to those skilled in the art.

The invention claimed is:

1. Apparatus for use in conjunction with a prosthetic heart valve comprising:
   a holder to which the heart valve is releasably attached, the holder comprising a main body portion and a rotatable portion; and
   an elongated handle having a distal end portion, the rotatable portion having a receptacle portion that is adapted to removably receive the distal end portion by relative non-rotational motion of the holder and handle along a longitudinal axis along which the handle is elongated, the receptacle portion defining an opening in a top surface of the holder, the opening configured to receive the distal end portion of the elongated handle, wherein the rotatable portion is assembled with the main body portion, such that the rotatable portion is translationally fixed along the longitudinal axis relative to the main body portion, and the rotational portion is rotatable about the longitudinal axis relative to the main body portion between an initial position and a final position, wherein the main body portion and the rotational portion each have a notch, the notches being configured to indicate whether or not the rotational portion is in the initial position, wherein the notch of the main body portion and the notch of the rotational portion are configured to be aligned in an axial direction parallel to the longitudinal axis when the rotational portion is in the initial position, and wherein the notch of the main body portion and the notch of the rotational portion are each visible from a location above the top surface of the holder.

2. The apparatus as claimed in claim 1 further comprising means for releasably latching the distal end portion into the receptacle portion.

3. The apparatus as claimed in claim 2 wherein the means for releasably latching is automatically responsive to reception of the distal end portion in the receptacle portion to latch the distal end portion in the receptacle portion.

4. The apparatus as claimed in claim 1 further comprising means for transmitting torque about said axis from the handle to a rotatable portion of the holder while the handle is received in the holder.

5. The apparatus as claimed in claim 4 wherein the rotatable portion of the holder comprises a mechanism for inwardly deflecting portions of the valve.

6. The apparatus as claimed in claim 5 wherein the mechanism limits the extent to which the portions of the valve can be inwardly deflected by the mechanism.

7. The apparatus as claimed in claim 6 wherein, after the mechanism has reached its limit of the extent to which the portions of the valve can be inwardly deflected by the mechanism, the mechanism transmits any further torque in either direction about said axis from the handle to structure of the holder other than the rotatable portion.

8. The apparatus as claimed in claim 5 wherein the mechanism is operable only in a direction in which it deflects the portions of the valve inwardly.

9. The apparatus as claimed in claim 5 wherein the mechanism maintains inward deflection of the portions of the valve that it has imparted to those portions even if the handle is separated from the holder.

10. The apparatus as claimed in claim 5 wherein the mechanism is operable on the portions of the valve through sutures that are connected between the mechanism and the portions of the valve.

11. The apparatus as claimed in claim 10 wherein the sutures are severable to release the portions of the valve from inward deflection by the mechanism.

12. The apparatus as claimed in claim 5 wherein the mechanism includes a pawl component and a ratchet component, one of those components being mounted on the rotatable portion, and the other of those components being mounted on a non-rotatable portion of the holder.

13. The apparatus as claimed in claim 4 wherein the means for transmitting torque comprises a non-circular cross section of the distal end portion.

14. The apparatus as claimed in claim 13 wherein the rotatable portion includes the receptacle portion, and wherein the means for transmitting torque further comprises a non-circular interior perimeter of the receptacle portion.

15. The apparatus as claimed in claim 14 wherein the non-circular cross section is receivable within the non-circular interior perimeter so that when the non-circular cross section is rotated about the axis, a side of that cross section transmits torque about that axis to a side of the perimeter.

16. The apparatus as claimed in claim 1 further comprising means for transmitting torque about said axis from the handle to the holder while the handle is received in the holder.

17. The apparatus as claimed in claim 16 wherein the means for transmitting torque is operable to transmit torque that is in either direction about said axis.

18. The apparatus as claimed in claim 16 wherein the means for transmitting torque comprises a non-circular cross section of the distal end portion and a non-circular interior perimeter of the receptacle portion.

19. The apparatus as claimed in claim 18 wherein the non-circular cross section is receivable within the non-circular interior perimeter so that when the non-circular cross section is rotated about the axis, a side of that cross section transmits torque about the axis to a side of the perimeter.

20. The apparatus as claimed in claim 1 wherein the notch of the main body portion is formed in an outer peripheral surface of the main body portion, and the notch of the rotational portion is formed in an outer peripheral surface of the rotational portion, the outer peripheral surface of the main body portion and the outer peripheral surface of the rotational portion each facing in a radial direction away from the longitudinal axis.

* * * * *